United States Patent [19]

Lindner et al.

[11] Patent Number: 4,600,574
[45] Date of Patent: Jul. 15, 1986

[54] METHOD OF PRODUCING A TISSUE ADHESIVE

[75] Inventors: Adolf Lindner; Yendra Linnau, both of Vienna, Austria

[73] Assignee: Immuno Aktiengesellschaft fur Chemisch-Medizinische Produkte, Vienna, Austria

[21] Appl. No.: 591,784

[22] Filed: Mar. 21, 1984

[51] Int. Cl.⁴ .............................................. A61K 9/70
[52] U.S. Cl. ....................................... 424/28; 424/27; 424/101; 514/801; 514/2
[58] Field of Search .................... 424/27, 101, 177, 28

[56] References Cited

U.S. PATENT DOCUMENTS

| | | | |
|---|---|---|---|
| 4,215,200 | 7/1980 | Miyata et al. | 424/27 |
| 4,265,233 | 5/1981 | Sugitachi et al. | 128/156 |
| 4,298,598 | 11/1981 | Schwarz et al. | |
| 4,362,567 | 12/1982 | Schwarz et al. | |
| 4,377,572 | 3/1983 | Schwarz et al. | |
| 4,442,655 | 4/1984 | Stroetmann | 424/27 |

Primary Examiner—Sam Rosen
Attorney, Agent, or Firm—Burns, Doane, Swecker & Mathis

[57] ABSTRACT

In a method of producing a tissue adhesive based on polysaccharide or on human or animal proteins, a tissue-compatible flat material is impregnated with a solution of fibrinogen and Factor XIII, and lyophilized.

7 Claims, No Drawings

METHOD OF PRODUCING A TISSUE ADHESIVE

The invention relates to a method of producing a tissue adhesive based on human or animal proteins having a content of fibrinogen and Factor XIII and, if desired, a content of a plasmin inhibitor, an antibiotic and a cytostatic.

It has been known to use blood clotting substances for stopping bleedings and for covering wounds. According to the first suggestions of this kind, fibrin tampons and fibrin platelets have been used. A method of producing tissue adhesives of fibrinogen and Factor XIII has been described in U.S. Pat. Nos. 4,362,567 and 4,298,598 and 4,377,572.

Furthermore, it is known to use tissue adhesives having a porous structure based on collagen for covering wounds, wherein a non-woven fabric consisting of collagen fibres is applied to the wound.

For fixing the collagen non-woven fabric, either a fibrinogen-thrombin-mixture was applied to the wound area or to the inner side of the collagen non-woven fabric, whereupon the non-woven fabric was pressed onto the wound. This method has, however, the disadvantage that the fibrinogen coagulates very rapidly due to the thrombin, and a penetration into the collagen is not possible. Also, it is very difficult to achieve an optimum timing of the fixing procedure with the help of the fibrinogen-thrombin mixture.

Furthermore, a material for healing wounds is known (German Offenlegungsschrift No. 29 14 822) which material has a fibrous structure, e.g., of collagen or of synthetic polymers, to which Factor XIII is fixed. This material is not suited as a wound adhesive, since it is only able to function with the cooperation of the coagulation-active factors present in the wound area. However, these factors are present in a slight amount only and therefore do not suffice.

The invention aims at avoiding these disadvantages and difficulties and has as its object to provide a method of the initially defined kind, by which a tissue adhesive can be formed such that it is applicable without limitations, i.e., that it can be used for stopping bleedings, covering wounds and uniting tissues, for the application of which no special preparation of the wound area is necessary and which guarantees a tighter wound cover or connection.

According to the invention, this object is achieved in that an aqueous mixture containing a tissue-compatible material, in particular collagen, gelatine or polysaccharide, as well as fibrinogen and Factor XIII is prepared and shaped to a plane structure, which under the formation of a flat material, such as a non-woven fabric or a sheet with a coherent matrix of a tissue-compatible material is lyophilized.

According to a preferred embodiment, the mixture and its shaping to a plane structure is effected by impregnating a porous collagen non-woven fabric with an aqueous solution containing fibrinogen and Factor XIII.

Suitably, a pre-fabricated porous collagen non-woven fabric is used.

Preferably, as the porous collagen non-woven fabric such a non-woven fabric is used which has been obtained by lyophilizing an aqueous solution of collagen in layers.

According to an advantageous embodiment, for a multi-layered formation of the flat material, the shaping of the mixture to a plane structure and its lyophilization are repeated at least once.

The method according to the invention will be explained in more detail in the following examples.

EXAMPLE 1

10 l of frozen human fresh plasma are heated to $+2°$ C., and the cryoprecipitate containing Factor XIII as well as fibrinogen is obtained by centrifugation.

The cold-soluble proteins are extracted from the cryoprecipitate by extraction with a buffer solution and removed. The remaining proteins are dissolved at 37° C. in 100 ml of a citrate-glycine buffer which contains aprotinin (2,500 KIU), heparin (20 IU) and amikacin sulfate (2,000 mg), and sterile filtered. The filtrate contains at least 1,000 units of Factor XIII and at least 7,500 mg of fibrinogen.

Commercially available collagen non-woven fabrics are partitioned into flat pieces having sizes of about 70 cm$^2$, and each flat piece is treated under sterile conditions with 15 ml of the Factor XIII and fibrinogen-containing solution. Thereupon the flat pieces are frozen, the swollen pieces are lyophilized and sterile packed.

Instead of using prefabricated collagen flat pieces or non-woven materials, the same can be formed in situ by lyophilization in a Petri dish, whereupon the impregnating procedure with a solution containing Factor XIII and fibrinogen is carried out as described above.

EXAMPLE 2

10 l of frozen human fresh plasma are heated to $+2°$ C., and the cryoprecipitate containing Factor XIII as well as fibrinogen is obtained by centrifugation.

The cold-soluble proteins are extracted from the cryoprecipitate by means of a buffer solution and removed. The remaining proteins are dissolved in 100 ml of a citrate-glycine buffer which contains aprotinin (2,500 KIU), heparin (20 IU) and amikacin sulfate (2,000 mg) and sterile filtered. The filtrate contains at least 1,000 units of Factor XIII and at least 7,500 mg of fibrinogen.

To this mixture is added under sterile conditions 100 ml of sterile 1% collagen solution. Thereupon this mixture is partitioned into 20 ml portions and distributed into Petri dishes, layers having a thickness of 2 to 5 mm being formed. Then the portions present in the Petri dishes are frozen and lyophilized, porous flat structures forming. They are sterile packed in the Petri dishes as the final containers. When applied, they are taken from the Petri dishes and laid onto the wound region.

EXAMPLE 3

In the same manner as described in Example 1, the protein base material containing Faxtor XIII and fibrinogen is obtained from frozen human fresh plasma by obtaining the cryoprecipitate and separation of the cold-soluble proteins, is dissolved in a citrate-glycine-buffer containing C$_1$-inactivator (35 PU), heparin (20 IU) and glutamin sulfate (2,500 mg), and is sterile filtered.

To the dissolving buffer, additional amounts of Factor XIII up to twice the amount of the natively contained amount may be added, which is preferred if an antibiotic is contained.

To this mixture there is added under sterile conditions the same amount of a commercially available 3.5% gelatine solution. Subsequently the mixture is shaped to flat structures in Petri dishes, as described in Example 1, the swollen pieces are lyophilized and sterile packed.

EXAMPLE 4

Obtaining the protein base material containing Factor XIII and fibrinogen is effected in the same manner as in Examples 1 and 2, and so is the dissolving and sterile filtration of the citrate-glycine-buffer solution. To the filtrate the same amount of a 6% hydroxy ethylene starch is admixed, the mixture is portioned into Petri dishes and shaped to flat structures, whereupon it is frozen, lyophilized and sterile packed.

What we claim is:

1. A method of producing a tissue adhesive based on polysaccharide or on human or animal proteins, said method comprising the steps of (a) impregnating a tissue-compatible flat material selected from the group consisting of collagen, gelatine and polysaccharide with a solution comprised of fibrinogen and Factor XIII, and (b) lyophilizing said impregnated flat material to obtain a coherent matrix of said tissue-compatible flat material.

2. A method as set forth in claim 1, wherein said tissue-compatible flat material comprises a non-woven fabric or sheet based on a material selected from the group consisting of collagen, gelatine and polysaccharide.

3. A method as set forth in claim 1, wherein said solution for impregnating said tissue-compatible, flat material further comprises at least one of a plasmin inhibitor, an antibiotic or a cytostatic agent.

4. A method of producing a tissue adhesive based on human or animal proteins, said method comprising the steps of
   (a) producing a flat material by lyophilizing an aqueous solution of collagen to layers so as to obtain a porous collagen flat material.
   (b) impregnating said porous collagen flat material with a solution comprised of fibrinogen and Factor XIII, and
   (c) lyophilizing said impregnated collagen flat material to obtain a coherent matrix of said collagen flat material.

5. A method of producing a tissue adhesive based on human or animal proteins, said method comprising lyophilizing an aqueous solution of fibrinogen, collagen and Factor XIII in layers so as to form a flat material containing fibrinogen, Factor XIII and collagen.

6. A method as set forth in claim 5, wherein said aqueous solution further comprises at least one of a plasmin inhibitor, an antibiotic or a cytostatic agent.

7. A method as set forth in claim 5, further comprising the step of repeating at least once the lyophilizing of aqueous solution of fibrinogen, collagen and factor XIII on the previously formed flat material to form a multi-layered flat material.

* * * * *

UNITED STATES PATENT AND TRADEMARK OFFICE
CERTIFICATE OF CORRECTION

PATENT NO. : 4,600,574
DATED : July 15, 1986
INVENTOR(S) : Adolf Lindner and Yendra Linnau It is certified that error appears in the above-identified patent and that said Letters Patent is hereby corrected as shown below:

Column 4, line 7, "to" (first occurrence) should read

-- in --.

Signed and Sealed this

Twenty-second Day of September, 1987

Attest:

DONALD J. QUIGG

Attesting Officer     Commissioner of Patents and Trademarks